United States Patent
Pan et al.

(10) Patent No.: US 10,695,278 B2
(45) Date of Patent: *Jun. 30, 2020

(54) PHOTO-STABILIZED COMPOSITIONS AND METHODS OF USE

(71) Applicant: L'OREAL, Paris (FR)

(72) Inventors: Zhi Pan, Ridgewood, NJ (US); Paul Mortizen, Livingston, NJ (US); Marie-Lise Chiron, Paris (FR); Karine Lucet-Levannier, Paris (FR)

(73) Assignee: L'OREAL, Paris (FR)

(*) Notice: Subject to any disclaimer, the term of this patent is extended or adjusted under 35 U.S.C. 154(b) by 227 days.

This patent is subject to a terminal disclaimer.

(21) Appl. No.: 15/087,694

(22) Filed: Mar. 31, 2016

(65) Prior Publication Data

US 2017/0281505 A1    Oct. 5, 2017

(51) Int. Cl.
| | |
|---|---|
| *A61K 8/60* | (2006.01) |
| *A61K 8/34* | (2006.01) |
| *A61K 8/49* | (2006.01) |
| *A61Q 19/08* | (2006.01) |
| *A61Q 19/02* | (2006.01) |
| *A61Q 17/04* | (2006.01) |
| *A61K 8/58* | (2006.01) |
| *A61Q 19/00* | (2006.01) |

(52) U.S. Cl.
CPC ............ *A61K 8/602* (2013.01); *A61K 8/347* (2013.01); *A61K 8/498* (2013.01); *A61Q 19/00* (2013.01); *A61Q 19/02* (2013.01); *A61Q 19/08* (2013.01); *A61K 2800/49* (2013.01); *A61K 2800/522* (2013.01); *A61Q 17/04* (2013.01)

(58) Field of Classification Search
None
See application file for complete search history.

(56) References Cited

U.S. PATENT DOCUMENTS

| | | |
|---|---|---|
| 4,820,508 A | 4/1989 | Wortzman |
| 4,828,825 A | 5/1989 | Weber et al. |
| 5,952,391 A | 9/1999 | Gers-Barlag et al. |
| 6,264,995 B1 | 7/2001 | Newmark et al. |
| 6,409,996 B1 | 6/2002 | Plaschke |
| 8,115,033 B2 | 2/2012 | Koch et al. |
| 8,263,051 B2 | 9/2012 | Bonda et al. |
| 8,580,319 B2 | 11/2013 | Cheng et al. |
| 9,072,919 B2 | 7/2015 | Pan et al. |
| 2007/0009455 A1 | 1/2007 | Kim et al. |
| 2008/0213200 A1 | 9/2008 | Vromen |
| 2009/0208434 A1 | 8/2009 | Schmaus et al. |
| 2010/0204343 A1 | 8/2010 | Koch et al. |
| 2012/0015015 A1 | 1/2012 | Kim et al. |
| 2012/0231097 A1 | 9/2012 | Zhou et al. |
| 2013/0078205 A1 | 3/2013 | Dayan et al. |
| 2013/0315848 A1 | 11/2013 | Beck et al. |
| 2013/0324616 A1 | 12/2013 | Beck et al. |
| 2014/0134120 A1* | 5/2014 | Jouy ............... A61K 8/4966 424/59 |
| 2015/0005247 A1* | 1/2015 | Chen .............. A61K 8/347 514/27 |
| 2015/0359715 A1 | 12/2015 | Chevalier et al. |

FOREIGN PATENT DOCUMENTS

| | | |
|---|---|---|
| CN | 101357114 A | 2/2009 |
| CN | 102258434 A | 11/2011 |
| CN | 103221024 A | 7/2013 |
| CN | 103221025 A | 7/2013 |
| CN | 104958247 A | 10/2015 |
| EP | 1263403 A1 | 12/2002 |
| EP | 2545898 A1 | 1/2013 |
| EP | 2642972 A1 | 10/2013 |
| EP | 2642973 A1 | 10/2013 |
| EP | 2679243 A1 | 1/2014 |
| WO | WO-96/18380 A1 | 6/1996 |
| WO | WO-2004050050 A1 | 6/2004 |
| WO | WO-2012069362 A1 | 5/2012 |
| WO | WO-2012069363 A1 | 5/2012 |
| WO | WO-2013007829 A2 | 1/2013 |

OTHER PUBLICATIONS

Giampietro Ravagnan, A. De Filippis, M. Carteni, S. De Maria, V. Cozza, M. Petrazzuolo, M. A. Tufano, G. Donnarumma. "Polydatin, A Natural Precursor of Resveratrol, Induces β-Defensin Production and Reduces Inflammatory Response". Inflamm. Feb. 2013, vol. 36, pp. 26-34 (Year: 2013).*
Wang HL, Gao JP, Han YL, Xu X, Wu R, Gao Y, Cui XH. "Comparative studies of polydatin and resveratrol on mutual transformation and antioxidative effect in vivo", Phytomedicine. May 15, 2015;22(5):553-9. Epub Apr. 6, 2015 (Year: 2015).*
(Min, Wet al.) "The effects of baicalin against UVA-induced photoaging in skin fibroblasts." The American Journal of Chinese Medicine. 2014, vol. 42, No. 03; 709-727.
(Farris, P et al.) "Evaluation of efficacy and tolerance of a nighttime topical antioxidant containing resveratrol, baicalin, and vitamin a for treatment of mild to moderately photodamaged skin." Journal of Drugs in Dermatology: JDD. 2014, vol. 13, No. 12; abstract.
(Amri, A, et al.) "Administration of resveratrol: what formulation solutions to bioavailability limitations?." Journal of Controlled Release. 2012, vol. 158, No. 2; p. 183.
Notification of Transmittal of the International Search Report and the Written Opinion of the International Search Authority, or the Declaration, International Application No. PCT/US17/24029.
Supplementary European Search Report dated Dec. 12, 2019 for corresponding European Application No. 17776350.

(Continued)

*Primary Examiner* — Nicole P Babson
(74) *Attorney, Agent, or Firm* — Polsinelli PC

(57) ABSTRACT

The present disclosure relates to cosmetic compositions and methods of using the cosmetic compositions to benefit the skin. The cosmetic compositions typically include: (a) resveratrol, polydatin, or a mixture thereof; (b) baicalin; (c) optionally, one or more solubilizers; and (d) a cosmetically acceptable carrier. The compositions provide multiple benefits to skin. For example, the compositions are particularly useful for providing anti-aging benefits to skin, for whitening the skin, and for improving skin's appears (e.g., radiance and firmness).

17 Claims, 4 Drawing Sheets

(56) References Cited

OTHER PUBLICATIONS

Chen Zheng-Guang et al: "Antiviral effects of Jinxin oral liquid against respiratory syncytial virus infection in the BALB/c mice model", Journal of Ethnopharmacology, vol. 162, 2015, pp. 287-295, XP029198317.
Dai Hong-Feng et al: "Simultaneous determination of three components in compound Hu-huang spray by UPLC", Nanjing Zhongyiyao Daxue Xuebao (2014), vol. 30,No. 1, 2014,pp. 88-89, XP009517507.
Jin Kyung Seok et al: "Scutellaria radix Extract as a Natural UV Protectant for Human Skin : UV Protection by Scutellaria radix Extract", Phytotherapy Research., vol. 30, No. 3, 2016, pp. 374-379, XP055526242.
Bing-Rong Zhou et al: "Protective effect of baicalin against multiple ultraviolet B exposure-mediated injuries in C576L/6 mouse skin", Archives of Pharmacal Research, vol. 34, No. 2, 2012, pp. 261-268, XP002670690.

\* cited by examiner

US 10,695,278 B2

PHOTO-STABILIZED COMPOSITIONS AND METHODS OF USE

FIELD OF THE DISCLOSURE

The present disclosure relates to cosmetic compositions and methods of using the compositions to benefit skin. The compositions improve the appearance of skin and provide multiple benefits to the skin such as, for example, anti-aging benefits.

BACKGROUND

Skin acts as a natural barrier between internal and external environments and therefore plays an important role in vital biological functions such as protection against mechanical and chemical injury, micro-organisms, and ultraviolet damage. The health and appearance of skin, however, can deteriorate due to environmental factors, genetic makeup, nutrition, and sun exposure.

With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively impact the skin, causing dryness, rash, and puffiness.

The formation of free radicals is a one widely accepted pivotal mechanism leading to skin aging. Free radicals are highly reactive molecules with unpaired electrons that can directly damage various cellular membranes, lipids, proteins, RNA and DNA. The damaging effects of these reactive oxygen species are induced internally during normal metabolism and externally through various oxidative stresses. UV exposure and environmental pollution can accelerate skin aging by producing free radicals in skin.

SUMMARY OF THE DISCLOSURE

The instant disclosure relates to cosmetic compositions and methods of using the compositions to benefit skin. The compositions improve the appearance of skin and provide multiple anti-aging and other benefits to the skin. The compositions are unique in their ability to photostabilize resveratrol, polydatin, and combinations thereof. The inventors surprisingly found that baicalin unexpectedly improves the photostability of resveratrol, polydatin, and mixtures thereof.

The compositions of the instant disclosure typically include: (a) resveratrol, polydatin, or a mixture thereof; (b) baicalin; (c) optionally, one or more solubilizers; and (d) a cosmetically acceptable carrier; wherein the baicalin of (b) improves the photostability of the resveratrol, polydatin, or mixture thereof. For example, in some cases, baicalin improves the photostability of the resveratrol, polydatin, or a mixture thereof, by at least 5%, relative to an otherwise identical composition without baicalin.

In some instances, the compositions include the one or more solubilizers of (c), which can be, for example, one or more cosmetically acceptable hydrotopes. A non-limiting list of possible hydrotropes include nicotinamide, caffeine, sodium PCA, sodium salicylate, urea, and hydroxyethyl urea.

The compositions of the instant disclosure in some cases include (e) one or more emulsifiers, which may be amphoteric, anionic, cationic, nonionic, or a mixture thereof. Moreover, the compositions may be in the form of an emulsion.

Other non-limiting components that can optionally be included in the compositions of the instant disclosure include, for example: (f) one or more UV filters; (g) one or more skin active ingredients; (h) one or more silicon oils; and (i) vitamin E;

As mentioned above, the compositions are unique in their ability to photostabilize resveratrol, polydatin, and combinations thereof. Accordingly, in some aspects, the instant disclosure relates to methods for photo-stabilizing resveratrol, polydatin, or a mixture thereof with baicalin, the method comprising combining the resveratrol, polydatin, or mixture thereof with baicalin in a cosmetically acceptable carrier; and optionally adding one or more solubilizers; thereby improving the photo-stability of the resveratrol, polydatin, or a mixture thereof.

Finally, the instant disclosure relates to methods of using the compositions described herein, for example, in the treatment of skin. The compositions may be used in methods for: providing anti-aging benefits to the skin; whitening or preventing darkening of skin; improving the appearance of skin; strengthening skin's natural antioxidant defenses; diminishing the visible signs of skin aging; and improving skin's radiance and firmness.

Figure 1:
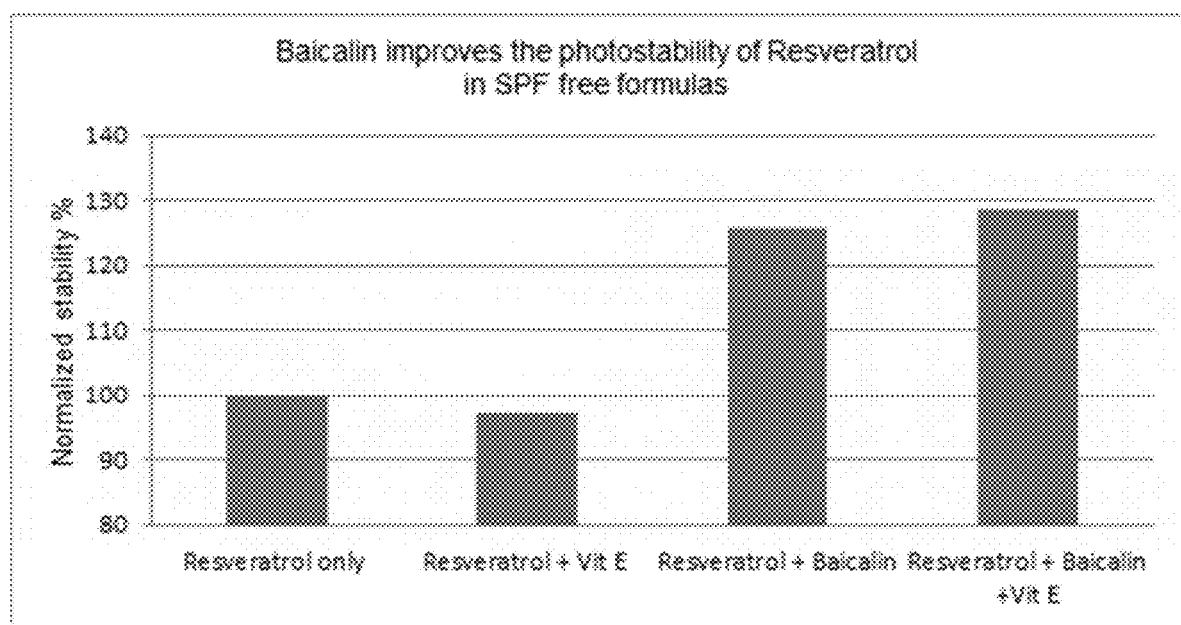
FIG. 1 is a graph showing baicalin's effect on the photostabiltiy of resveratrol in compositions without UV filters.

It should be understood that the various aspects are not limited to the arrangements and instrumentality shown in the figures.

DETAILED DESCRIPTION OF THE DISCLOSURE

The instant disclosure relates to cosmetic compositions comprising: (a) resveratrol, polydatin, or a mixture thereof; (b) baicalin; (c) optionally, one or more solubilizers; and (d) a cosmetically acceptable carrier. The baicalin of (b) unexpectedly improves the photostability of the resveratrol, polydatin, or mixture thereof. For example, in some cases, baicalin improves the photostability of the resveratrol, polydatin, or a mixture thereof, by at least 5%, relative to an otherwise identical composition without baicalin. Likewise, in some cases, the baicalin improves the photostability of the compositions by at least about 6%, about 8%, about 10%, about 12%, about 14%, about 16%, about 18%, about 20%, about 22%, about 24%, about 26%, about 28%, about 30%, or more. Often, the degree of improvement in photostability may depend on the amount of baicalin present in the compositions, i.e., baicalin appears to provide dose-dependent effect. Although the degree of improvement in photostability is not limited, in some cases, should an upper limit be required, the improvement in photostability may be any one of the minimum values set forth above up to and upper limit of, for example, about 30%, about 32%, about 34% about 35%, about 38%, about 40, or about 50%.

The total amount of the resveratrol, polydatin, or mixture thereof of (a) in the compositions may be, for example, about 0.001 to about 10 wt. %, based on the total weight of the composition. In some instances, the total amount of resveratrol, polydatin, or mixture thereof in the compositions may be about 0.001 wt. % to about 9 wt. %, about 8 wt. %, about 7 wt. %, about 6 wt. %, about 5 wt. %, about 4 wt. %, about 3 wt. %, or about 2 wt. %. Likewise, in some instances the total amount of the resveratrol, polydatin, or mixture thereof in the compositions may be about 0.01 wt. % to about 9 wt. %, about 8 wt. %, about 7 wt. %, about 6 wt. %, about 5 wt. %, about 4 wt. %, about 3 wt. %, or about 2 wt. %. Additionally, the total amount of the resveratrol, polydatin, or mixture thereof in the compositions may be about 0.1 wt. % to about 9 wt. %, about 8 wt. %, about 7 wt. %, about 6 wt. %, about 5 wt. %, about 4 wt. %, about 3 wt. %, or about 2 wt. %. Finally, the total amount of the resveratrol, polydatin, or mixture thereof in the compositions may be about 0.5 wt. % to about 5 wt. %, about 0.5 wt. % to about 3 wt. %, 0.5 wt. % to about 2 wt. %, or about 1 wt. %.

The total amount of the baicalin of (b) in the compositions may be, for example, about 0.001 wt. % to about 12 wt. %, based on the total weight of the composition. In some instances, the total amount of baicalin in the compositions may be about 0.001 wt. % to about 12 wt. %, about 10 wt. %, about 8 wt. %, about 6 wt. %, about 4 wt. %, about 2 wt. %, or about 1 wt. %. Likewise, in some cases, the total amount of baicalin in the compositions may be about 0.01 wt. % to about 12 wt. %, about 10 wt. %, about 8 wt. %, about 6 wt. %, about 4 wt. %, about 3 wt. %, about 2 wt. %, about 1 wt. %, or about 0.5 wt. %.

In some instances, the compositions include the one or more solubilizers (c). Various solubilizers are well known in the art and may be useful for the compositions described herein. In some cases, the one or more solubilizers can be, for example, one or more cosmetically acceptable hydrotopes. A non-limiting list of possible hydrotropes includes nicotinamide, caffeine, sodium PCA, sodium salicylate, urea, and hydroxyethyl urea. The total amount of the one or more hydrotropes in the composition may be about 0.001 wt. % to about 30 wt. %, based on the total weight of the composition. In some instances, the total amount of the one or more hydrotropes in the composition is about 0.001 wt. % to about 25 wt. %, about 20 wt. %, about 15 wt. %, about 14 wt. %, about 12 wt. %, about 10 wt. %, about 8 wt. %, about 6 wt. %, about 4 wt. %, or about 2 wt. %. Likewise, in some instances the total amount of the one or more solubilizers in the compositions may be about 0.01 wt. % to about 30 wt. %, 25 wt. %, 20 wt. %, 15 wt. %, about 14 wt. % about 12 wt. %, about 10 wt. %, about 8 wt. %, about 6 wt. %, about 4 wt. %, or about 2 wt. %. Moreover, the total amount of the one or more solubilizers in the composition may be about 0.1 wt. % to about 30 wt. %, 25 wt. %, 20 wt. %, 15 wt. %, about 14 wt. % about 12 wt. %, about 10 wt. %, about 8 wt. %, about 6 wt. %, about 4 wt. %, or about 2 wt. %.

In some instances, if the composition includes at least the hydrotrope hydroxyethyl urea, the maximum amount of the one or more hydrotropes in the composition may be higher than 30 wt. %. For example, if the hydrotrope hydroxyethyl urea is present in the composition, the total amount of the one or more hydrotropes may be (in addition to the ranges already set forth in the above paragraph), from about 1 wt. % to about 60 wt. %, from about 5 wt. % to about 60 wt. %, from about 5 wt. % to about 55 wt. %, from about 5 wt. % to about 50 wt. %, from about 10 wt. % to about 60 wt. %, from about 10 wt. % to about 55 wt. %, from about 10 wt. % to about 50 wt. %, from about 20 wt. % to about 60 wt. %, from about 20 wt. % to about 55 wt. %, from about 20 wt. % to about 50 wt. %, or from about 25 wt. % to about 55 wt. %.

As mentioned previously, the instant compositions typically include a cosmetically acceptable carrier (c), which can also optionally function to solubilize components of the compositions. For example, the cosmetically acceptable carrier may include water, an organic solvent, or a mixture thereof. Moreover, the cosmetically acceptable carrier may comprise, for example, a hydrophilic organic solvent and/or an amphiphilic organic solvent, wherein the hydrophilic organic solvent is a monohydric $C_1$-$C_8$ alcohol, a polyethylene glycol having from 6 to 80 ethylene oxides, and/or a mono or di-alkyl isosorbide; and the amphiphilic organic solvent is a polypropylene glycol (PPG) and/or a propylene glycol alkyl ester and/or alkyl ether of PPG. Non-limiting examples include ethanol, methanol, PEG 8, propylene glycol, dipropylene glycol, buytlene glycol, and isopropyl lauroyl sarccosinate.

In some instances, the compositions of the instant disclosure include the one or more emulsifiers (e). Many emulsifiers are known in the art, which may be used in the instant compositions, including, amphoteric, anionic, cationic, and nonionic emulsifiers. Non-limiting examples of nonionic emulsifiers include polyol esters, a glycerol ethers, oxyethylenated and/or oxypropylenated ethers, ethylene glycol polymers, and mixtures thereof. For example, in some cases the emulsifier includes a mixture of a polyol ester and an ethylene glycol polymer, for example, a mixture of glyceryl stearate and PEG-100 stearate. In some instances, an oxyalkylenated organosiloxane emulsifier is included. Non-limiting examples include dimethicone/PEG-10/15 crosspolymer, PEG-15 lauryl dimethicone crosspolymer, PEG-15 lauryl dimethicone crosspolymer, PEG-10 lauryl dimethicone crosspolymer, or a mixture thereof. Accordingly, the compositions of the instant disclosure are often, but not necessarily, in the form of an emulsion.

The total amount of the one or more emulsifiers, when present, may be, for example, about 0.001 to about 10 wt. %, based on the total weight of the composition. In some instances, the total amount of the one or more emulsifiers in the compositions may be about 0.001 wt. % to about 9 wt. %, about 8 wt. %, about 7 wt. %, about 6 wt. %, about 5 wt. %, about 4 wt. %, about 3 wt. %, or about 2 wt. %. Likewise, in some instances the total amount of one or more emulsifiers in the compositions may be about 0.01 wt. % to about 9 wt. %, about 8 wt. %, about 7 wt. %, about 6 wt. %, about 5 wt. %, about 4 wt. %, about 3 wt. %, or about 2 wt. %. Additionally, the total amount of the one or more emulsifiers in the compositions may be about 0.1 wt. % to about 9 wt. %, about 8 wt. %, about 7 wt. %, about 6 wt. %, about 5 wt. %, about 4 wt. %, about 3 wt. %, or about 2 wt. %. Finally, the total amount of the one or more emulsifiers in the compositions may be about 0.5 wt. % to about 5 wt. %, about 0.5 wt. % to about 3 wt. %, 0.5 wt. % to about 2 wt. %, or about 1 wt. %.

In some instances, the compositions of the instant disclosure include one or more UV filters (f). Many UV filters are known in the art, which may be used in the instant compositions. The UV filter may be a single UV filter, or a combination of two, three, four, five, or more UV filters, including organic and/or inorganic UV filters. In some instances, the UV filter is an organic UV filter. The one or more UV filters may be selected from the group consisting of a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof.

In some cases, the one or more UV filters is in an amount of from 0.001 wt. % to about 30 wt. %, about 0.001 to about 20 wt. %, 0.001 to about 10 wt. %, about 0.1 to about 30 wt. %, about 0.1 wt. % to about 25 wt. %, about 0.1 to about 20 wt. %, about 0.1 to about 18 wt. %, 0.1 to about 15 wt. %, about 0.1 to about 12 wt. %, about 0.1 to about 10 wt. %, 0.1 to about 8 wt. %, about 0.1 to about 6 wt. %, about 1 wt. % to about 30 wt. %, about 0.1 wt. % to about 25 wt. %, about 1 wt. % to about 20 wt. %, about 1 wt. % to about 18 wt. %, about 1 wt. % to about 15 wt. %, about 1 wt. % to about 12 wt. %, about 1 wt. % to about 10 wt. %, about 1 wt. % to about 8 wt. %, about 1 wt. % to about 6 wt. %, about 5 wt. % to about 30 wt. %, about 5 wt. % to about 25 wt. %, about 5 wt. % to about 20 wt. %, about 5 wt. % to about 18 wt. %, about 5 wt % to about 15 wt. %, about 5 wt. % to about 12 wt. %, about 5 wt. % to about 10 wt. %, about 5 wt. % to about 8 wt. %, or from about 3 wt. % to about 20 wt. %, wherein the weight percent is based on the total weight of the sunscreen composition.

In some instances, the compositions of the instant disclosure include one or more skin active ingredients (g). For example, the skin active ingredient may be a humectant, a moisturizing ingredient, an anti-aging agent, a depigmenting agent, an anti-wrinkle agent, an agent that treats oily skin, and a mixture thereof. In some cases, the one or more skin active ingredients may be adenosine, ascorbic acid, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, or a mixture thereof.

The amount of the skin active ingredients may be individual or combination from about 0.001 to about 10 wt. %, based on the total weight of the composition. In some instances, the amount of the skin active ingredients may be individual or combination from about 0.001 wt. % to about 9 wt. %, about 8 wt. %, about 7 wt. %, about 6 wt. %, about 5 wt. %, about 4 wt. %, about 3 wt. %, or about 2 wt. %. Likewise, in some instances the amount of the skin active ingredients may be individual or combination from about 0.01 wt. % to about 9 wt. %, about 8 wt. %, about 7 wt. %, about 6 wt. %, about 5 wt. %, about 4 wt. %, about 3 wt. %, or about 2 wt. %. Additionally, the amount of the skin active ingredients may be individual or combination from 0.1 wt. % to about 9 wt. %, about 8 wt. %, about 7 wt. %, about 6 wt. %, about 5 wt. %, about 4 wt. %, about 3 wt. %, or about 2 wt. %. Finally, the amount of the skin active ingredients may be individual or combination from about 0.5 wt. % to about 5 wt. %, about 0.5 wt. % to about 3 wt. %, 0.5 wt. % to about 2 wt. %, or about 1 wt. %.

In some instances, the compositions of the instant disclosure include one or more silicon oils (h). For example, the one or more silicon oils may be selected from the group consisting of polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl (trimethylsiloxy)diphenylsiloxanes, diphenyl dimethicones, diphenyl(methyldiphenyl)trisiloxanes, (2-phenylethyl) trimethyl siloxysilicates, and a mixture thereof. In some cases, the one or more silicon oils comprises dimethicone. The total amount of the one or more silicon oils may be, for example, from about 0.1 wt. % to about 40 wt. %, about 35 wt. %, about 30 wt. %, about 25 wt. %, about 20 wt. %, about 15 wt. %, about 10 wt. %, about 5 wt. %, about 4 wt. %, about 3 wt. %, or about 2 wt. %. In some cases, the total amount of silicon oil may be from about 0.1 wt. %, about 0.5 wt. %, about 1 wt. %, about 2 wt. %, about 3 wt. %, about 4 wt. %, about 5 wt. %, about 10 wt. %, about 15 wt. % to about 40 wt. %.

In some cases, the compositions of the instant disclosure include vitamin E (i). The total amount of the vitamin E of (i) in the compositions may be about 0.001 to about 10 wt. %, based on the total weight of the composition. In some instances, the total amount of vitamin E in the compositions may be about 0.001 wt. % to about 9 wt. %, about 8 wt. %, about 7 wt. %, about 6 wt. %, about 5 wt. %, about 4 wt. %, about 3 wt. %, or about 2 wt. %. Likewise, in some instances the total amount of vitamin E in the compositions may be about 0.01 wt. % to about 9 wt. %, about 8 wt. %, about 7 wt. %, about 6 wt. %, about 5 wt. %, about 4 wt. %, about 3 wt. %, or about 2 wt. %. Additionally, the total amount of vitamin E in the compositions may be about 0.1 wt. % to about 9 wt. %, about 8 wt. %, about 7 wt. %, about 6 wt. %, about 5 wt. %, about 4 wt. %, about 3 wt. %, or about 2 wt. %.

The compositions described herein are unique in their ability to photostabilize resveratrol, polydatin, and combinations thereof. Accordingly, in some aspects, the instant disclosure relates to methods for photo-stabilizing resveratrol, polydatin, or a mixture thereof with baicalin, the method comprising combining the resveratrol, polydatin, or mixture thereof with baicalin in a cosmetically acceptable carrier; and optionally adding one or more solubilizers; thereby improving the photo-stability of the resveratrol, polydatin, or a mixture thereof. For example, in some cases, baicalin improves the photostability of the resveratrol, polydatin, or a mixture thereof, by at least 5%, relative to an otherwise identical composition without baicalin. Likewise, in some cases, the baicalin improves the photostability of the compositions by at least about 6%, about 8%, about 10%, about 12%, about 14%, about 16%, about 18%, about 20%, about 22%, about 24%, about 26%, about 28%, about 30%, or more. Often, the degree of improvement in photostability may depend on the amount of baicalin present in the compositions, i.e., baicalin appears to provide dose-dependent effect. Although the degree of improvement in photostability is not limited, in some cases, should an upper limit be required, the improvement in photostability may be any one of the minimum values set forth above up to and upper limit of, for example, about 30%, about 32%, about 34% about 35%, about 38%, about 40, or about 50%.

Finally, the instant disclosure relates to methods of using the compositions described herein, for example, in the treatment of skin. The compositions may be used in methods for: providing anti-aging benefits to the skin; whitening or preventing darkening of skin; improving the appearance of skin; strengthening skin's natural antioxidant defenses; diminishing the visible signs of skin aging; and improving skin's radiance and firmness. These methods typically entail applying the compositions described herein to the skin.

More exhaustive but non-limiting lists of components useful in the compositions disclosed herein are presented below.

Solubilizers

The solubilizers are typically compounds or groups of compounds that help solubilize the resveratrol, the polydatin, and/or the baicalin in the compositions of the instant disclosure. One or more solubilizers may be a hydrotrotrope, but the solubilizers are not required to be hydrotropes. Hydrotropes (or hydrotropic agents) are a diverse class of water-soluble compounds that are characterized by an amphiphilic molecular structure and an ability to dramatically increase the solubility of poorly soluble organic molecules in water.

Many hydrotropes have an aromatic structure with an ionic moiety, while some of them are linear alkyl chains. Although hydrotropes noticeably resemble surfactants and have the ability to reduce surface tension, their small hydrophobic units and relatively shorter alkyl chain distinguish them as a separate class of amphiphiles. Consequently their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinamide, N-picolylnicotinamide, N-allylnicotinamide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003; and Lee S. et al., "Hydrotropic Polymers: Synthesis and Characterization of Polymers Containing Picolylnicotinamide Moieties", Macromolecules, 36, 2248-2255, 2003. Additional hydrotropes include nicotinamide (Vit B3), caffeine, sodium PCA, sodium salicylate, urea, an dihydroxyethyl urea.

Cosmetically Acceptable Carrier

Cosmetically acceptable carriers include, but are not limited to, one or more aqueous systems, glycerin, $C_{1-4}$ alcohols, organic solvents, fatty alcohols, fatty ethers, fatty esters, polyols, glycols, vegetable oils, mineral oils, liposomes, laminar lipid materials, water, or any combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Emulsifiers

Emulsifiers are well known in the art and include amphoteric, anionic, cationic or nonionic emulsifiers, used alone or as a mixture, and optionally with a co-emulsifier. The emulsifiers are chosen in an appropriate manner according to the emulsion to be obtained.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

In some instance, the one or more emulsifiers include an oganosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In another embodiment, the compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

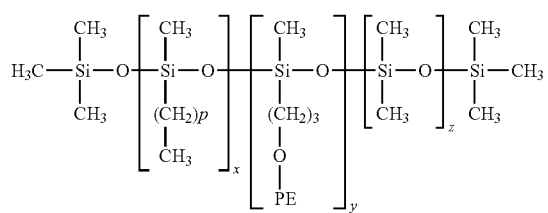

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

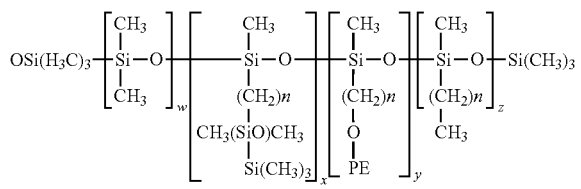

wherein each n is independently 0-100 with the proviso that there must be at least one PE radical. In some instances, where each n independently ranges from about 2 to 30, and PE $(-C_2H_4O)_a-(-C_3H_6O)_b-H$ wherein a is 0-25, b is 0-25 with the proviso that both a and b cannot simultaneously be 0; and wherein w, x, y, and z are each independently 0 to 1,000,000 with the proviso that there is at least one PE. In some embodiments the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially cross-linked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used in at least one embodiment include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

UV Filters.

UV filters are well known in the art for their use in stopping UV radiation. For example, the UV filter may be one or more organic UV filters and/or one or more inorganic UV filters. Non-limiting examples of UV filters include:
  i. Sparingly soluble UV filters (not appreciably soluble in either water or oil) such as Methylene Bis-Benzotriazolyl Tetramethylbutylphenol, Tris-Biphenyl Triazine, Methanone, 1,1'-(1,4-piperazinediyl)bis[1-[2-[4-(diethylamino)-2-hydroxybenzoyl]phen-yl]—and mixtures thereof.
  ii. Oil soluble organic UV filters (at least partially soluble in oil or organic solvent), such as Bis-Ethylhexyloxyphenol Methoxyphenyl Triazine, Butyl Methoxydibenzoylmethane (BMBM), Oxybenzone, Sulisobenzone, Diethylhexyl Butamido Triazone (DBT), Drometrizole Trisiloxane, Ethylhexyl Methoxycinnamate (EHMC), Ethylhexyl Salicylate (EHS), Ethylhexyl Triazone (EHT), Homosalate, Isoamyl p-Methoxycinnamate, 4-Methylbenzylidene Camphor, Octocrylene (OCR), Polysilicone-15, and Diethylamino Hydroxy Benzoyl Hexyl Benzoate (DHHB);
  iii. Inorganic UV filters such as titanium oxide and zinc oxide, iron oxide, zirconium oxide and cerium oxide; and
  iv. Water soluble UV filters such as Phenylbenzimidazole Sulfonic Acid (PBSA), Sulisobenzone-sodium salt, Benzydilene Camphor Sulfonic Acid, Camphor Benzalkonium Methosulfate, Cinoxate, Disodium Phenyl Dibenzylmidazole Tetrasulfonate, Terephthalylidene Dicamphor Sulfonic Acid, PABA, and PEG-25 PABA.

In some instances, the UV filter is one or more of: a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, or a mixture thereof.

Suitable UV filters can include broad-spectrum UV filters that protect against both UVA and UVB radiation, or UV filters that protect against UVA or UVB radiation. In some instances, the one or more UV filters may be methylene bis-benzotriazolyl tetramethylphenol, diethylamino hydroxybenzoyl hexyl benzoate, coated or uncoated zinc oxide, ethylhexyl methoxycinnamate, isoamyl methoxycinnamate, homosalate ethyl hexyl salicilate, octocrylene, polysilicone-15, butyl methoxydibenzoylmethane, menthyl anthranilate, and ethylhexyl dimethyl PABA.

Furthermore, combinations of UV filters may be used. For example, the combination of UV filters may be octocrylene, avobenzone (butyl methoxydibenzoylmethane), oxybenzone (benzophenone-3), octisalate (ethylhexyl salicylate), and homosalate, as described in application Ser. No. 13/304,195, which is incorporated herein by reference in its entirety. For instance, this combination of UV filters may be used in the following ratios relative to avobenzone:
  the ratio of octocrylene to avobenzone is 1.6:1.0 to 2.4:1.0;
  the ratio of oxybenzone to avobenzone 1.0:1.0 to 1.6:1.0;
  the ratio of octisalate to avobenzone is 0.8:1.0 to 1.3:1.0; and
  the ratio of homosalate to avobenzone is 2.8:1.0 to 4.3:1.

Furthermore, the ratio of each UV filter relative to avobenzone may be about: 2.0:1.0:1.3:1.1:3.6 (octocrylene: avobenzone:oxybenzone:octisalate:homosalate).

In another embodiment, the at least one UV filter is a combination of UV filters comprising octocrylene, avobenzone, octisalate, and homosalate, and optionally oxybenzone, as described in application Ser. No. 13/304,202, which is incorporated herein by reference in its entirety. For instance, this combination of UV filters may be used in the following ratios relative to avobenzone:
  the ratio of octocrylene to avobenzone is 1.6:1.0 to 2.4:1.0,
  the ratio of oxybenzone to avobenzone 0.0:1.0 to 0.016:1.0,
  the ratio of octisalate to avobenzone is 1.3:1.0 to 2.0:1.0, and
  the ratio of homosalate to avobenzone is 2.3:1.0 to 3.6:1.

Furthermore, the ratio of each UV filter relative to avobenzone may be about: 2.0:1.0:0.0:1.7:3.0 (octocrylene: avobenzone:oxybenzone:octisalate:homosalate).

In another embodiment, the at least one UV filter is a combination of UV filters comprising octocrylene, butyl methoxydibenzoylmethane, bis-ethylhexyloxyphenol methoxyphenyl triazine, ethylhexyl triazone, terephthalylidene dicamphor sulfonic acid, and drometrizole trisiloxane, as described in application Ser. No. 13/719,328, which is incorporated herein by reference in its entirety. For instance, this combination of UV filters may be used in the following ratios relative to butyl methoxydibenzoylmethane:

the ratio of octocrylene to butyl methoxydibenzoylmethane is 0.8:1.0 to 1.5:1.0;

the ratio of bis-ethylhexyloxyphenol methoxyphenyl triazine to butyl methoxydibenzoylmethane 0.3:1.0 to 0.8:1.0;

the ratio of ethylhexyl triazone to butyl methoxydibenzoylmethane is 0.3:1.0 to 1.0:1.0;

the ratio of terephthalylidene dicamphor sulfonic acid to butyl methoxydibenzoylmethane is 0.1:1.0 to 0.5:1.0; and the ratio of drometrizole trisiloxane to butyl methoxydibenzoylmethane is 0.3:1.0 to 1.0:1.0.

Furthermore, the ratio of each UV filter relative to butyl methoxydibenzoylmethane may be about: 1.2:1.0:0.5:0.6:0.4:0.6 (octocrylene:butyl methoxydibenzoylmethane:bis-ethylhexyloxyphenol methoxyphenyl triazine:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, ethylhexyl triazone, terephthalylidene dicamphor sulfonic acid, and drometrizole trisiloxane, as described in application Ser. No. 13/719,351, which is incorporated herein by reference in its entirety. For instance, this combination of UV filters may be used in the following ratios relative to butyl methoxydibenzoylmethane:

the ratio of octocrylene to butyl methoxydibenzoylmethane is 0.6:1.0 to 1.25:1.0;

the ratio of ethylhexyl triazone to butyl methoxydibenzoylmethane is 0.4:1.0 to 1.0:1.0;

the ratio of terephthalylidene dicamphor sulfonic acid to butyl methoxydibenzoylmethane is 0.3:1.0 to 0.7:1.0; and the ratio of drometrizole trisiloxane to butyl methoxydibenzoylmethane is 0.4:1.0 to 1.1:1.0.

Furthermore, the ratio of each UV filter relative to butyl methoxydibenzoylmethane may be about: 1.0:1.0:0.7:0.5:0.7 (octocrylene:butyl methoxydibenzoylmethane:ethylhexyl triazone:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,368, which is incorporated herein by reference in its entirety. For instance, this combination of UV filters may be used in the following ratios relative to butyl methoxydibenzoylmethane:

the ratio of octocrylene to butyl methoxydibenzoylmethane is 0.8:1.0 to 1.2:1.0;

the ratio of bis-ethylhexyloxyphenol methoxyphenyl triazine to butyl methoxydibenzoylmethane is 0.2:1.0 to 0.6:1.0;

the ratio of terephthalylidene dicamphor sulfonic acid to butyl methoxydibenzoylmethane is 0.0.25:1.0 to 0.75:1.0; and the ratio of drometrizole trisiloxane to butyl methoxydibenzoylmethane is 0.4:1.0 to 0.8:1.0.

Furthermore, the ratio of each UV filter relative to butyl methoxydibenzoylmethane may be about: 1.0:1.0:0.4:0.4:0.6 (octocrylene:butyl methoxydibenzoylmethane:bis-ethylhexyloxyphenol methoxyphenyl triazine:terephthalylidene dicamphor sulfonic acid:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and drometrizole trisiloxane, as described in application Ser. No. 13/719,374, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.3:1.0;

the ratio of bis-ethylhexyloxyphenol methoxyphenyl triazine to butyl methoxydibenzoylmethane is 0.1:1.0 to 0.6:1.0;

the ratio of ethylhexyl triazone to butyl methoxydibenzoylmethane is 0.2:1.0 to 0.6:1.0; and the ratio of drometrizole trisiloxane to butyl methoxydibenzoylmethane is 0.3:1.0 to 0.7:1.0. [Synergistic combination from PR2012573]

Furthermore, the ratio of each UV filter relative to butyl methoxydibenzoylmethane may be about: 1.0:1.0:0.3:0.5:0.5 (octocrylene:butyl methoxydibenzoylmethane:bis-ethylhexyloxyphenol methoxyphenyl triazine:ethylhexyl triazone:drometrizole trisiloxane).

In another embodiment, the at least one UV filter is a combination of UV filters comprising octocrylene, butyl methoxydibenzoylmethane, bis-ethylhexyloxyphenol methoxyphenyl triazine, terephthalylidene dicamphor sulfonic acid, and terephthalylidene dicampohor sulfonic acid, as described in application Ser. No. 13/719,393, which is incorporated herein by reference in its entirety. For instance, this combination of UV filters may be used in the following ratios relative to butyl methoxydibenzoylmethane is as follows:

the ratio of octocrylene to butyl methoxydibenzoylmethane is 0.8:1.0 to 1.6:1.0;

the ratio of bis-ethylhexyloxyphenol methoxyphenyl triazine to butyl methoxydibenzoylmethane is 0.2:1.0 to 0.6:1.0;

the ratio of ethylhexyl triazone to butyl methoxydibenzoylmethane is 0.3:1.0 to 0.6:1.0; and the ratio of terephthalylidene dicampohor sulfonic acid to butyl methoxydibenzoylmethane is 0.01:1.0 to 0.3:1.0.

Furthermore, the ratio of each UV filter relative to butyl methoxydibenzoylmethane may be about: 1.2:1.0:0.3:0.5:0.1 (octocrylene:butyl methoxydibenzoylmethane:bis-ethylhexyloxyphenol methoxyphenyl triazine:ethylhexyl triazone:terephthalylidene dicampohor sulfonic acid).

Silicon Oils.

Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes ($8\times10^6$ m$^2$/s) and especially containing from 2 to 7 silicon atoms, these silicones optionally comprising alkyl or alkoxy groups containing from 1 to 10 carbon atoms. As volatile silicone oils that may be used in the disclosure, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Implementation of the present disclosure is provided by way of the following examples. The examples serve to illustrate the technology without being limiting in nature.

EXAMPLES

Example 1

Photostability of Resveratrol

Four formulations comprising resveratrol (Formulations A-D) were prepared and the photostability of the resveratrol measured.

| Phase | Ingredient | A Resveratrol | B Resveratrol Vitamin E | C Resveratrol Baicalin | D Resveratrol Baicalin Vitamin E |
|---|---|---|---|---|---|
| A | Dimethicone | 15.5 | 15.5 | 15.5 | 15.5 |
|   | Dimethicone (and) PEG/PPG-18/18 Dimethicone | 7 | 7 | 7 | 7 |
| B | Water | 43.4 | 42.4 | 42.9 | 41.9 |
|   | Disodium EDTA | 0.1 | 0.1 | 0.1 | 0.1 |
|   | Sodium Chloride | 2 | 2 | 2 | 2 |
|   | Niacinamide | 5 | 5 | 5 | 5 |
|   | Caffeine | 2 | 2 | 2 | 2 |
|   | Baicalin | — | — | 0.5 | 0.5 |
|   | Glycerin | 3 | 3 | 3 | 3 |
| C | Propylene Glycol | 9 | 9 | 9 | 9 |
|   | Dipropylene Glycol | 7 | 7 | 7 | 7 |
|   | Resveratrol | 1 | 1 | 1 | 1 |
|   | Denat. Alcohol | 5 | 5 | 5 | 5 |
| D | Vitamin E | — | 1 | — | 1 |
|   | TOTAL | 100 | 100 | 100 | 100 |

Each of the four formulations (Formulations A-D) in the table above was a gel in the form of an inverse emulsion and was prepared by first mixing the components of phase A together. The components of phase B were individually added into the water component of phase B and mixed until the solution was clear. The clear solution of phase B was then added to phase A and the mixture was homogenized at room temperature until a uniform texture was achieved. The components of phase C were separately combined and mixed. The components of phase C can be slightly heated if necessary to obtain a clear solution. Finally, the clear solution of phase C is added to the mixture of A and B and homogenized at room temperature until a uniform texture is achieved.

The photostability of the resveratrol in each of the formulations was evaluated. A thin film (10 mg/cm$^2$) of each of the Formulas A-D were subjected to a dose of UVA radiation (5 J/cm$^2$). The residual amount of the resveratrol after exposure to the UVA radiation was determined by HPLC. The percentage of resveratrol after exposure was determined by comparing the residual amount of the resveratrol after exposure to the UVA radiation to the residual amount of the resveratrol under the same conditions but not treated with UVA radiation. In order to avoid the impact of variation from different UV lamps and different studies, the data was normalized for each study by the photostability of resveratrol or polydatin by themselves. Comparisons were always carried out in the same base formulas, with and without the addition of baicalin. The results are provided in the table below and graphically shown in FIG. 1.

| Formula | Actives | Relative Photostability (%) |
|---|---|---|
| A | Resveratrol | 100 |
| B | Resveratrol + Vitamin E | 97.1 |
| C | Resveratrol + Baicalin | 125.7 |
| D | Resveratrol + Baicalin + Vitamin E | 128.6 |

Example 2

Photostability of Polydatin

Four formulations comprising polydatin (Formulations E-H) were prepared and the photostability of the polyldatin measured.

| Phase | Ingredient | E Polydatin | F Polydatin Vitamin E | G Polydatin Baicalin | H Polyldating Baicalin Vitamin E |
|---|---|---|---|---|---|
| A | Dimethicone | 15.5 | 15.5 | 15.5 | 15.5 |
|   | Dimethicone (and) PEG/PPG-18/18 Dimethicone | 7 | 7 | 7 | 7 |
| B | Water | 43.4 | 42.4 | 42.9 | 41.9 |
|   | Disodium EDTA | 0.1 | 0.1 | 0.1 | 0.1 |

-continued

| Phase | Ingredient | E Polydatin | F Polydatin Vitamin E | G Polydatin Baicalin | H Polyldating Baicalin Vitamin E |
|---|---|---|---|---|---|
|   | Sodium Chloride | 2 | 2 | 2 | 2 |
|   | Niacinamide | 5 | 5 | 5 | 5 |
|   | Caffeine | 2 | 2 | 2 | 2 |
|   | Baicalin | — | — | 0.5 | 0.5 |
|   | Glycerin | 3 | 3 | 3 | 3 |
| C | Propylene Glycol | 9 | 9 | 9 | 9 |
|   | Dipropylene Glycol | 7 | 7 | 7 | 7 |
|   | Polydatin | 1 | 1 | 1 | 1 |
|   | Denat. Alcohol | 5 | 5 | 5 | 5 |
| D | Vitamin E | — | 1 | — | 1 |
|   | TOTAL | 100 | 100 | 100 | 100 |

Figure 2:
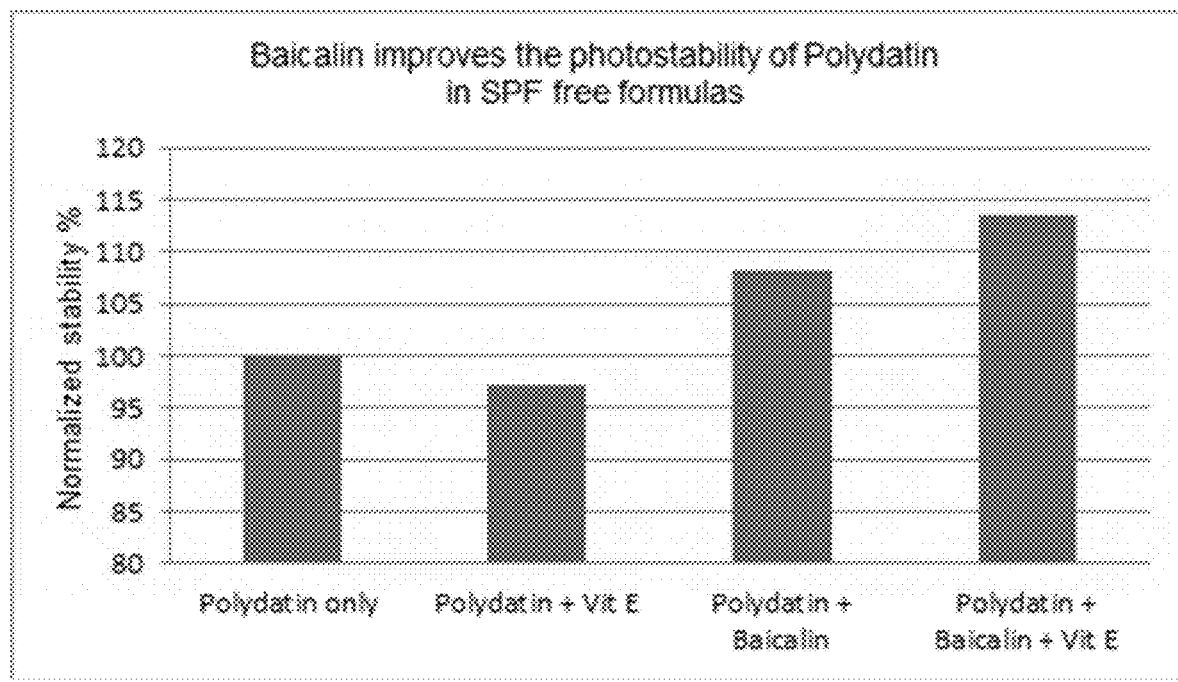
FIG. 2 is a graph showing baicalin's effect on the photostability of polydatin in compositions without UV filters.

Each of the four formulations (Formulations E-H) in the table above was a gel in the form of an inverse emulsion. The formulations were prepared in the same manner the formulations in Example 1 were prepared and the photostability of the polydatin was determined in the same manner the photostability of resveratrol was determined in Example 1. The results are provided in the table below and graphically shown in FIG. 2.

| Formula | Actives | Relative Photostability (%) |
|---|---|---|
| E | Polydatin | 100 |
| F | Polydatin + Vitamin E | 97.3 |
| G | Polydatin + Baicalin | 108.1 |
| H | Polydatin + Baicalin + Vitamin E | 113.5 |

Example 3

Photostability of Polydatin and Resveratrol

| Phase | Ingredient | I Polydatin | J Polydatin Baicalin |
|---|---|---|---|
| A1 | Water | QS | QS |
|   | Caprylyl Glycol | 0.3 | 0.3 |
|   | Preservative | 0.7 | 0.7 |
|   | Disodium EDTA | 0.2 | 0.2 |
|   | Baicalin | — | 0.5 |
|   | Caffeine | 3 | 3 |
|   | Niacinamide | 2 | 2 |
| A2 | Propylene Glycol | 7.5 | 7.5 |
|   | Dipropylene Glycol | 7.5 | 7.5 |
|   | Resveratrol | — | — |
|   | Polydatin | 1 | 1 |
|   | Xanthan Gum | 0.25 | 0.25 |
| B | Dicaprylyl Carbonate | 0.5 | 0.5 |
|   | Combination of UV filters | 20 | 20 |
|   | Stearic Acid | 1 | 1 |
|   | Nonionic emulsifers | 3 | 3 |
|   | Preservative | 0.5 | 0.5 |
|   | Dimethicone | 2 | 2 |
| C | Dimethicone (and) Dimethicone/Vinyl dimethicone Crosspolymer | 1 | 1 |
| D | Ammonium Polyacrloydimethyl Taurate | 0.57 | 0.57 |
| E | Water | 3 | 3 |
| F | Silica | 3 | 3 |

-continued

| Phase | Ingredient | I Polydatin | J Polydatin Baicalin |
|---|---|---|---|
| G | Mica (and) Titanium Dioxide (and) Red 28 Lake (and) Tin Oxide | 0.02 | 0.02 |
| H | Vitamin E | 1 | 1 |
| I | Fragrance | 0.4 | 0.4 |

Each of the two formulations (Formulation 1-J) was a cream in the form of an oil-in-water emulsion. The formulations were prepared by combining the components of Phase A and heating them to 75° C. while mixing. Separately, the components of Phase B were combined and heated to 75-80° C. while mixing. Then, Phase B was slowly added to Phase A over a period of 15 minutes and then homogenized the combination for 15 minutes. Once the temperature has dropped close to room temperature, Phase C was added at a temperature below 50° C. while mixing and then the mixture (containing Phases A, B and C) was homogenized for 10 minutes. The remaining Phases D, E, F, G, H and I were individually added to the mixture in the same manner as Phase C, i.e., the temperatures of the mixture was allowed to drop to close to room temperature, and then each phase was added at a temperature below 50° C. while mixing; and then the mixture was homogenized for 10 minutes.

Figure 3:
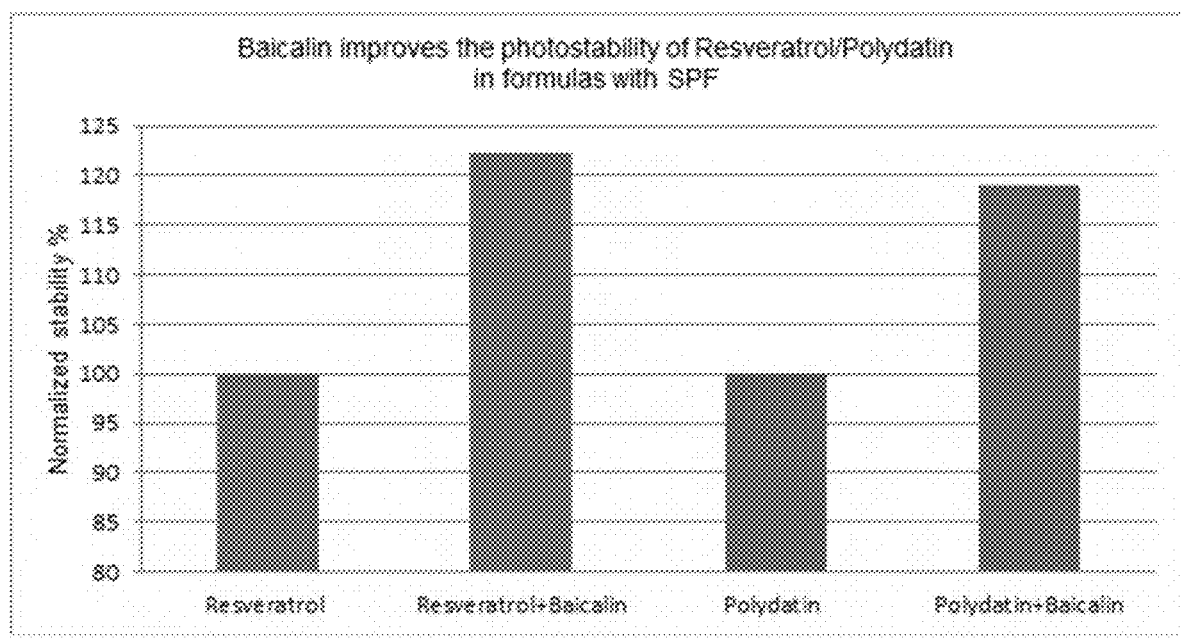
FIG. 3 is a is a graph showing baicalin's effect on the photostability of resveratrol and polydatin in compositions containing UV filters.

The photostability of polydatin in the formulations above (Formulations I and J) and the photostability of resveratrol in two formulations that were similar to the formulations above (Formulation K and L, which are not shown in the table above) was measured in the same manner as described in Example 1. The results are presented in the table below and are graphically shown in FIG. 3.

| Formula | Actives | Relative Photostability (%) |
|---|---|---|
| I | Polydatin | 100 |
| J | Polydatin + Baicalin | 119.0 |
| K | Resveratrol | 100 |
| L | Resveratrol + Baicalin | 122.4 |

Example 4

Dose Effect of Baicalin

Figure 4:
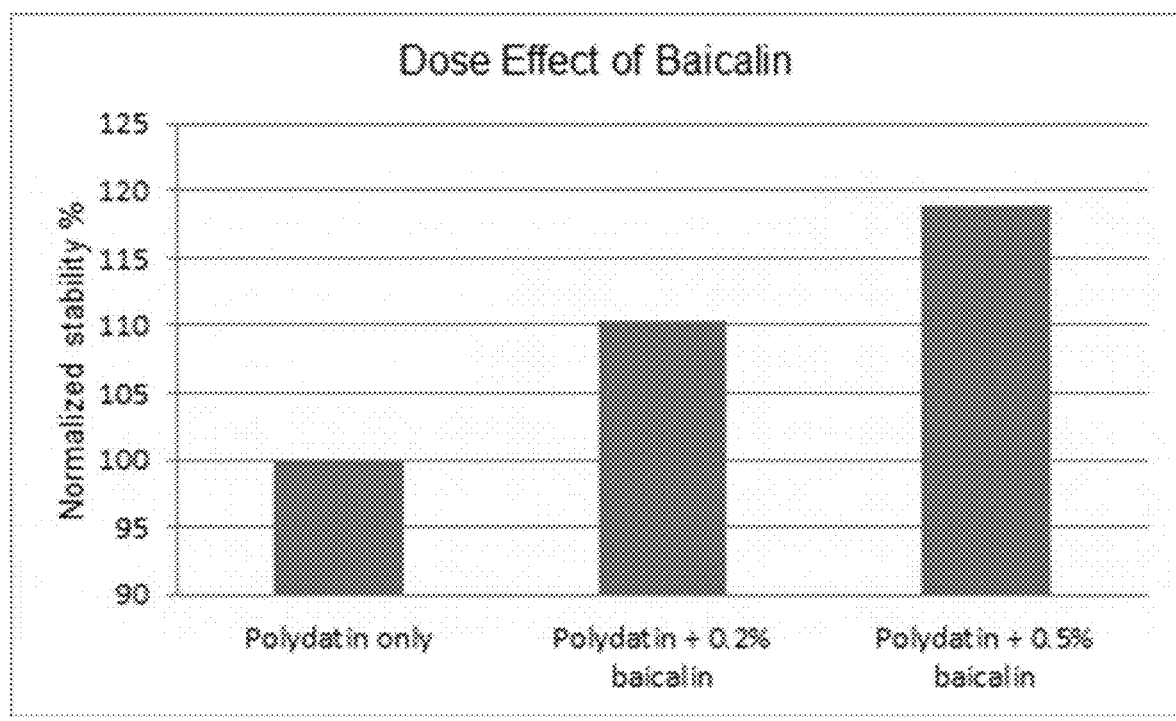
FIG. 4 is a graph showing the dose effect of baicalin on the photostability of polydatin.

To determine the dose effect of baicalin, the formula base described in Example 3 was used with different concentrations of baicalin and the photostability tested. The results are provided in the table below and graphically shown in FIG. 4.

| Formula | Actives | Relative Photostability (%) |
| --- | --- | --- |
| M | Polydatin Only | 100 |
| N | Polydatin + 0.2% Baicalin | 110.3 |
| O | Polydatin + 0.5% Baicalin | 119.0 |

The terms "a," "an," and "the" are understood to encompass the plural as well as the singular.

The expression "at least one" means "one or more" and vice versa, and thus includes individual components as well as mixtures/combinations.

The term "about" when referring to a value, is meant specifically that a measurement can be rounded to the value using a standard convention for rounding numbers. For example, "about 1.5" is 1.45 to 1.54. All values set forth herein can be modified with the term "about" or recited without the term, regardless of whether the term "about" is specifically set forth (or is absent) in conjunction with any particular value.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising;
   (a) 0.5 to 5 wt. %, based on the total weight of the composition, of polydatin;
   (b) 0.5 to 5 wt. %, based on the total weight of the composition, of baicalin;
   (c) optionally, one or more solubilizers;
   (d) a cosmetically acceptable carrier; and
   (i) 0.1 to 5 wt. %, based on the total weight of the composition, of vitamin E,
   wherein the baicalin of (b) improves the photostability of the polydatin of (a) by at least 5%, relative to an otherwise identical composition without baicalin; and the cosmetic composition is free of resveratrol.

2. The composition of claim 1 comprising the one or more solubilizers of (c).

3. The composition of claim 2, wherein the one or more solubilizers of (c) comprises one or more cosmetically acceptable hydrotropes selected from the group consisting of nicotinamide, caffeine, sodium PCA, sodium salicylate, urea, hydroxyethyl urea, and mixtures thereof.

4. The composition of claim 1, further comprising:
   (e) one or more emulsifiers.

5. The composition of claim 4, wherein the total amount of the one or more emulsifiers of (e) in the composition is 0.001 to 10 wt. %, based on the total weight of the composition.

6. The composition of claim 4, wherein the one or more emulsifiers of (e) comprises a nonionic emulsifier.

7. The composition of claim 6, wherein the nonionic emulsifier is selected from a polyol ester, a glycerol ether, an oxyethylenated ether, an oxypropylenated ether, an ethylene glycol polymer, and mixtures thereof.

8. The composition of claim 6, wherein the nonionic emulsifer comprises a mixture of a polyol ester and an ethylene glycol polymer.

9. The composition of claim 1, further comprising:
   (f) one or more UV filters.

10. The composition of claim 9, wherein the one or more UV filters of (f) are selected from the group consisting of a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and a mixture thereof.

11. The composition of claim 1, wherein the cosmetically acceptable carrier of (d) comprises water, an organic solvent, or a mixture thereof.

12. The composition of claim 1, further comprising:
   (g) one or more skin active ingredients.

13. The composition of claim 1, wherein the composition further comprises: (h) one or more silicone oils.

14. The composition of claim 13, wherein the one or more silicone oils of (h) are selected from the group consisting of polydimethylsiloxanes (PDMSs), polydimethylsiloxanes comprising alkyl or alkoxy groups which are pendent and/or at the end of the silicone chain, which groups each contain from 2 to 24 carbon atoms, phenyl silicones, and a mixture thereof.

15. The composition of claim 14, wherein the one or more silicone oils of (h) comprises dimethicone.

16. The composition of claim 1, comprising 0.1 wt. % to 3 wt. % of vitamin E.

17. A method for:
   providing anti-aging benefits to skin;
   whitening or preventing darkening of skin;
   improving the appearance of skin;
   strengthening skin's natural antioxidant defenses;
   diminishing the visible signs of skin aging; or
   improving skin's radiance and firmness;
   comprising applying the composition of claim 1 to skin.

* * * * *